United States Patent
Giordano (10) Patent No.: US 9,615,860 B2
(45) Date of Patent: Apr. 11, 2017

(54) PLATES CONFIGURED TO RIGIDLY FIX FRAGMENTS OF A PARS INTERARTICULARIS TO ONE ANOTHER

(76) Inventor: Carl Pasquale Giordano, New Vernon, NJ (US)

(*) Notice: Subject to any disclaimer, the term of this patent is extended or adjusted under 35 U.S.C. 154(b) by 165 days.

(21) Appl. No.: 13/438,912

(22) Filed: Apr. 4, 2012

(65) Prior Publication Data

US 2013/0268009 A1   Oct. 10, 2013

(51) Int. Cl.
*A61B 17/70* (2006.01)

(52) U.S. Cl.
CPC .......... *A61B 17/7059* (2013.01); *Y10T 29/49* (2015.01)

(58) Field of Classification Search
CPC ................................................. A61B 17/7071
See application file for complete search history.

(56) References Cited

U.S. PATENT DOCUMENTS

| 5,352,224 | A | * | 10/1994 | Westermann | 606/286 |
| 6,093,188 | A | * | 7/2000 | Murray | 606/282 |
| 6,506,191 | B1 | * | 1/2003 | Joos | A61B 17/8033 |
| | | | | | 606/280 |
| 2004/0097925 | A1 | * | 5/2004 | Boehm, Jr. | A61B 17/7059 |
| | | | | | 606/914 |
| 2006/0235408 | A1 | * | 10/2006 | Wang | A61B 17/663 |
| | | | | | 606/281 |
| 2010/0082067 | A1 | * | 4/2010 | Kondrashov | A61B 17/7044 |
| | | | | | 606/264 |
| 2010/0179597 | A1 | * | 7/2010 | Henderson et al. | 606/264 |

* cited by examiner

*Primary Examiner* — Samuel Hanna
(74) *Attorney, Agent, or Firm* — Fox Rothschild LLP (57) ABSTRACT

An apparatus for securing a vertebra during healing of a fracture within a pars area of the vertebra is described. In certain embodiments, the apparatus is a plate that has an outer shape similar to a shape of a pedicle and/or lamina of the vertebra, and an inner section that facilitates access to the pars area when the plate is secured to the vertebra.

3 Claims, 9 Drawing Sheets

PLATES CONFIGURED TO RIGIDLY FIX FRAGMENTS OF A PARS INTERARTICULARIS TO ONE ANOTHER

BACKGROUND

Spondylolysis is a condition in which a crack or fracture occurs in rear portions of vertebrae of a patient's spinal column. The spinal column includes a ring of bone located at the middle and posterior portion of the spinal column that protects the spinal cord within the spinal column. The specific area that becomes cracked or fractured is known as the pars interarticularis, or pars, and is the area between a pedicle and lamina of a vertebra.

The crack or fracture, often known as a "pars fracture" or "pars defect," is generally caused by excessive or repeated strain to the pars area, although congenital effects may also cause a pars fracture. Spondylolysis commonly occurs in the lower back at lumbar vertebra number five (L5). For example, Spondyloysis may affect athletes that repeatedly bend backwards, such as athletes in gymnastics, karate, and/or football.

Under strain, a vertebra will initially add bone cells around an injured area. However, once the strain is too great, or too violent, a stress fracture will form in the vertebra. Such a fracture will often occur within the pars, and multiple and/or persistent fractures lead to a pars defect.

In some cases, a pars defect will occur on two sides of a vertebra. When this occurs, a vertebra may translate or move towards or away from neighboring vertebrae, leading to a condition know as Spondylolisthesis.

Figure 1A:
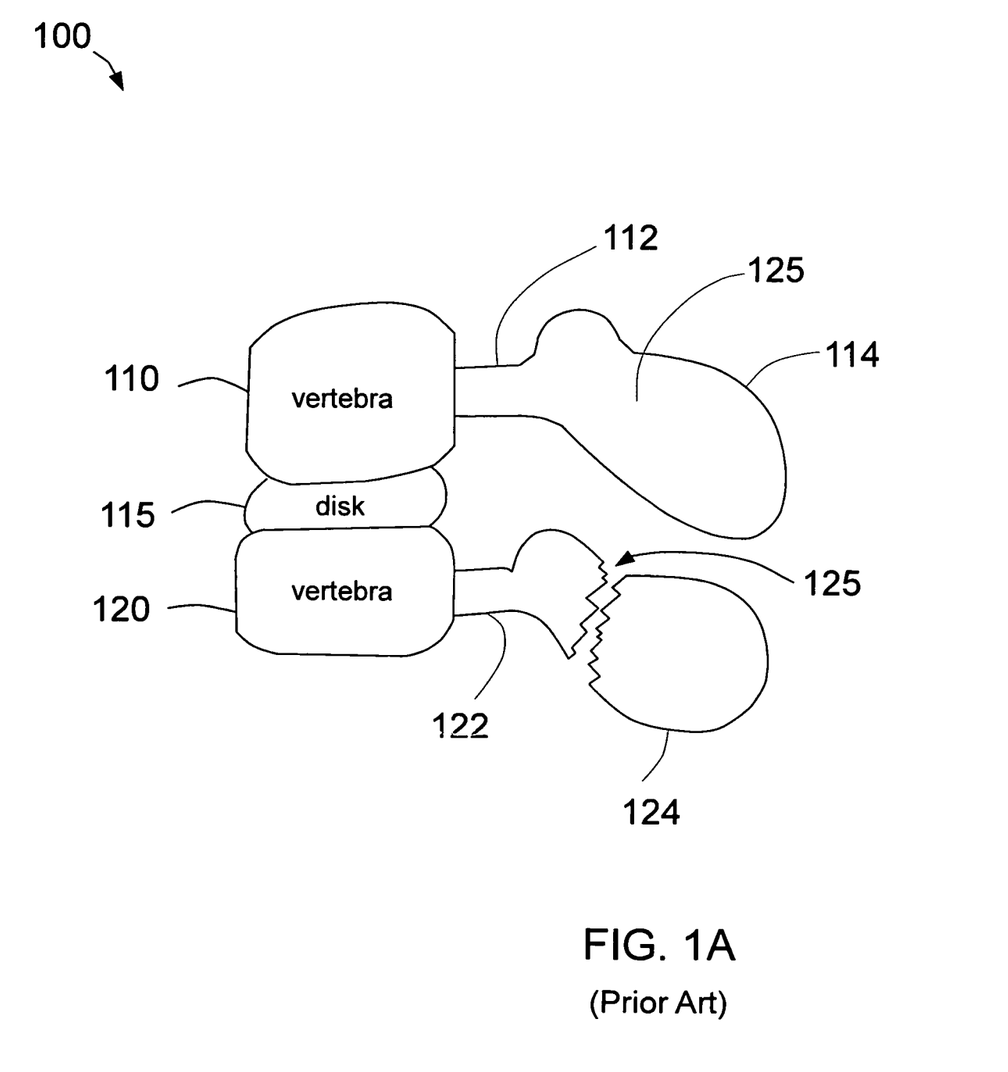
FIGS. 1A-1B are perspective views of common pars interarticularis areas having pars defects.
Figure 1B:
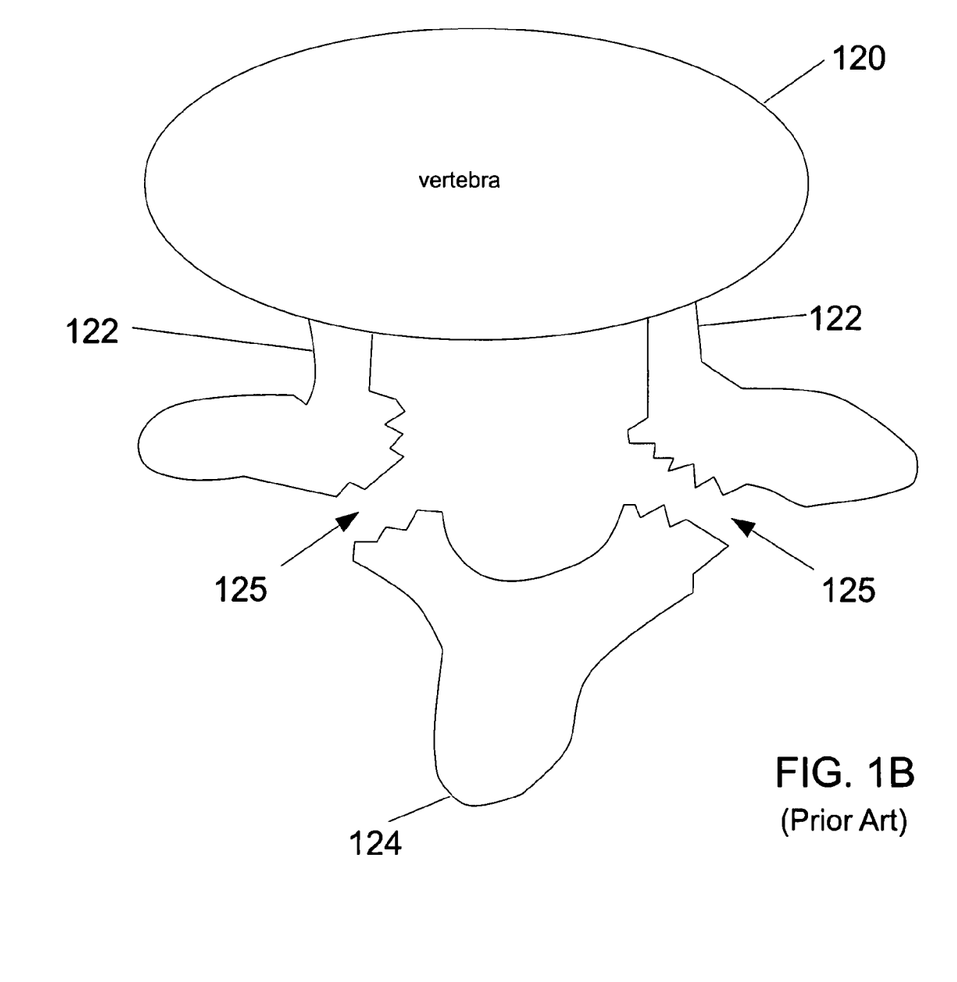

In order to illustrate where Spondyloysis occurs, FIGS. 1A-1B depict views of a pars fracture or defect within a vertebra. FIG. 1A illustrates a side view 100 of vertebrae of a spinal column. Vertebra 110 is separated from vertebra 120 by a disk 115. Vertebra 110 is a healthy vertebra, with a pedicle 112 and lamina 114 surrounding a pars area. In contrast, vertebra 120 in an unhealthy or affected vertebra, with a pedicle 122 and lamina 124 surrounding a pars fracture or defect 125. That is, the pars fracture 125 occurs in vertebra 120 between a pedicle 122 and lamina 124 of the vertebra.

FIG. 1B depicts the pars defect from another view, namely from a top view 130 of the vertebra 120. The pars fracture 125 is located between the pedicle 122 and the lamina 124, and may cause separation of the lamina 124 from the pedicle 122. Once separated, or partially separated, the lamina 124 may translate or move relative to the pedicle 122, causing pain and/or other problems.

Conventional treatment of Spondyloysis, Spondylolisthesis, and other conditions due to fractures in the pars interarticularis of a vertebra include (1) the fusing together of vertebral segments surrounding a pars fracture or (2) the attempting to repair the pars fracture. However, there are disadvantages with conventional treatments.

Fusing vertebral segments together often leads to a loss of motion across an affected area, which may cause additional stress to surrounding vertebrae and accelerate arthritis and other conditions within the vertebrae.

Conventional repair procedures, such as using wires or screws to hold vertebral fragments together, suffer from high failure rates, because the procedures often do not maintain fractured vertebral fragments in proper position during a bone grafting or other treatments.

In some cases, plates are used during surgical repairs within the spine. For example, a first reference, U.S. Published Patent Application No. 2010/0082067, to Kondrashov, entitled "System and Method to Stabilize a Spinal Column Including a Spinolaminar Locking Plate," discloses an anchoring plate adapted to stabilize a spinal column. The anchoring plate may have a shape that conforms to a lamina of a targeted vertebra, but is used and configured in order to stabilize a spinal column and reduce compression of spinal nerves.

As another example, a second reference, U.S. Published Patent Application No. 2005/0119657, to Goldsmith, entitled "Facet Triangle Spinal Fixation Device and Method of Use," discloses a device adapted to bilaterally secure two vertebrae together.

In both examples, the disclosed plates are generally utilized to stabilize a spinal column and proximate vertebrae within a spinal column.

While aforementioned medical devices and treatments are generally suitable for a particular purpose, such devices are not sufficiently suitable for the purpose discussed in the present invention. Thus, it is clear that there exists a need in the art for a treatment device that overcomes these problems and progresses the state of the art, as well as one that provides there additional benefits enumerated in the present application.

SUMMARY OF THE INVENTION

In view of the foregoing disadvantages inherent in the art, in accordance with a first preferred embodiment of the present invention, an apparatus configured and/or adapted to attach to a pars area of a vertebra is described. In some examples of the present invention, the plate is formed of a shape similar to a shape of a pedicle and/or lamina of the vertebra.

That is, in some embodiments, the plate may be configured to include an anatomical geometry similar to a geometry of an anatomical region in which the plate is attached during rigid fixation of a pars fracture. The geometry, or shape, may be similar to a geometry of a pedicle, a geometry of a lamina, or a geometry of both the pedicle and the lamina surrounding a pars fracture.

As mentioned, it is contemplated by the present disclosure that the plate may include an outer section that conforms to a shape of an attachment region, such as a pedicle and/or lamina, and an inner section that facilitates access to a fractured area when the plate is attached to a vertebra.

Furthermore, it is contemplated by the present disclosure that the plate include or be part of a support structure, and may include a fragment fixation section and a support section, whereby the plate provides for the rigid fixation of vertebral fragments and for the support of an affected vertebra.

Thus, in certain embodiments, the plate is configured and/or adapted to facilitate attachment to a pars area of a vertebra to provide rigid fixation during bone grafting and subsequent healing of a fracture within the pars area, while providing other inherent benefits.

By using the plates described herein, the success of repairing pars fractures and/or pars defects may be increased with respect to conventional approaches or treatment techniques.

Thus, there has been summarized and outlined, generally in broad form, a plurality of the most important features of the present invention. While this summary is presented so that the novelty of the present contribution to the related art may be better appreciated, it will further be apparent that additional features of the invention described hereinafter (which will form the subject matter of the claims appended hereto) will further define the scope, novelty, and in certain instances the improvements upon any existing art. The following description provides specific details for a thorough understanding of, and enabling description for, various examples of the technology. One skilled in the art will understand that the technology may be practiced without many of these details and it is to be readily understood that the invention presented herein is not limited in its application to the details of construction and to the arrangements of the components set forth in the following description or illustrated in the various figures integrated and categorized herein. For example, in some instances, well-known structures and functions have not been shown or described in detail to avoid unnecessarily obscuring the description of the examples of the technology. It is intended that the terminology used in the description presented below be interpreted in its broadest reasonable manner, even though it is being used in conjunction with a detailed description of certain examples of the technology. Although certain terms may be emphasized below, any terminology intended to be interpreted in any restricted manner will be overtly and specifically defined as such in this Detailed Description section. Those skilled in the art will appreciate that the disclosure of the present invention may readily be utilized as a basis for the designing of other similar structures, methods and systems for carrying out the various purposes and objectives of the present invention. Thus, the claims as set forth shall allow for such equivalent constructions insofar as they do not depart from the spirit and scope of the present invention as described herein.

BRIEF DESCRIPTION OF THE FIGURES OF THE PRESENT INVENTION

A further understanding of the present invention and the objectives other than those set forth above can be obtained by reference to the various embodiments set forth in the illustrations of the accompanying figures. Although the illustrated embodiments are merely exemplary of the present invention, apparatus and method of use of the invention, in general, together with further objectives and advantages thereof, may be more easily understood by reference to the drawings, examples, and the following description. The examples and figures are not intended to limit the scope of this invention, which is set forth with particularity in the claims as appended or as subsequently amended, but merely to clarify and exemplify the invention. The detailed description makes reference to the accompanying figures wherein:

DETAILED DESCRIPTION OF THE PRESENT INVENTION

A detailed illustrative embodiment of the present invention is disclosed herein. However, techniques of manufacture and resulting structures in accordance with the present invention may be embodied in a wide variety of forms and modes, some of which may be quite different from those in the disclosed embodiment. Consequently, the specific structural details disclosed herein are merely representative, yet in that regard, they are deemed to afford the best embodiment for purposes of disclosure and to provide a basis for the claims herein which define the scope of the present invention. The following presents a detailed description of several examples of the present invention.

Moreover, well known methods, procedures, and substances for both carrying out the objectives of the present invention and illustrating the preferred embodiment are incorporated herein but have not been described in detail as not to unnecessarily obscure novel aspects of the present invention.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The apparatus or device described herein (e.g., "pars plate") is a novel device configured to attach to a vertebra to assist during healing of a pars fracture of the vertebra. The pars plate may be formed in a shape similar to the vertebra or section of the vertebra in order to facilitate attachment and use within a compact and complexly structured area of the spinal column, and so on. Such a device may provide an alternative path for the treatment of pars fractures, among other benefits.

Figure 2:
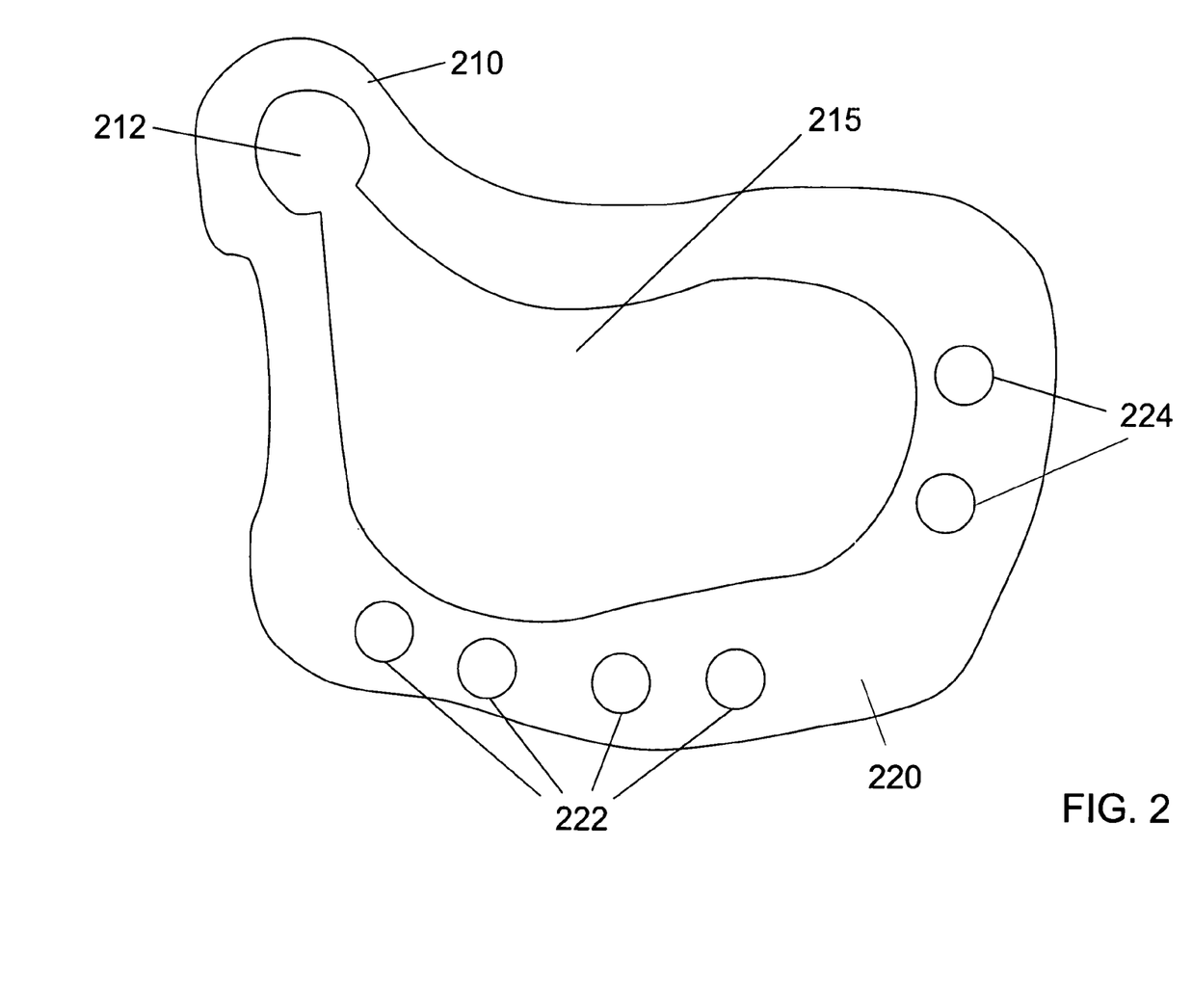
FIG. 2 is a perspective view of a plate configured to be attached to a pars area of a vertebra.

Turning to FIG. 2, provided is a perspective view of a plate configured to be attached to a pars area of a vertebra. The plate 200 includes a pedicle section 210 having a pedicle attachment hole 212 and a lamina section 220 having lamina attachment holes 222 and spinous process attachment holes 224. The attachment holes 212, 222, 224 may be configured to receive screws or other attachment devices that attach the plate 200 to a vertebra.

The plate 200 also includes an open section 215, which provides access to a fracture when the plate is attached to a pars area. The open section 215 may be configured as shown in the Figure, or may include an opening of various sizes and/or shapes, depending on the size and/or shape of the vertebra, the size and/or shape of the affected area of the vertebra, the size and/or shape of a fracture within the pars area, and so on.

The pedicle section 210 and lamina section 220 of the plate 200 may be formed having an I-beam cross section, and are adapted to conform to the shape of the pars area in which the plate 200 is attached. The shape of the plate 200 will now be discussed with respect to the shape of a vertebra in which the plate 200 is attached.

Figure 3:
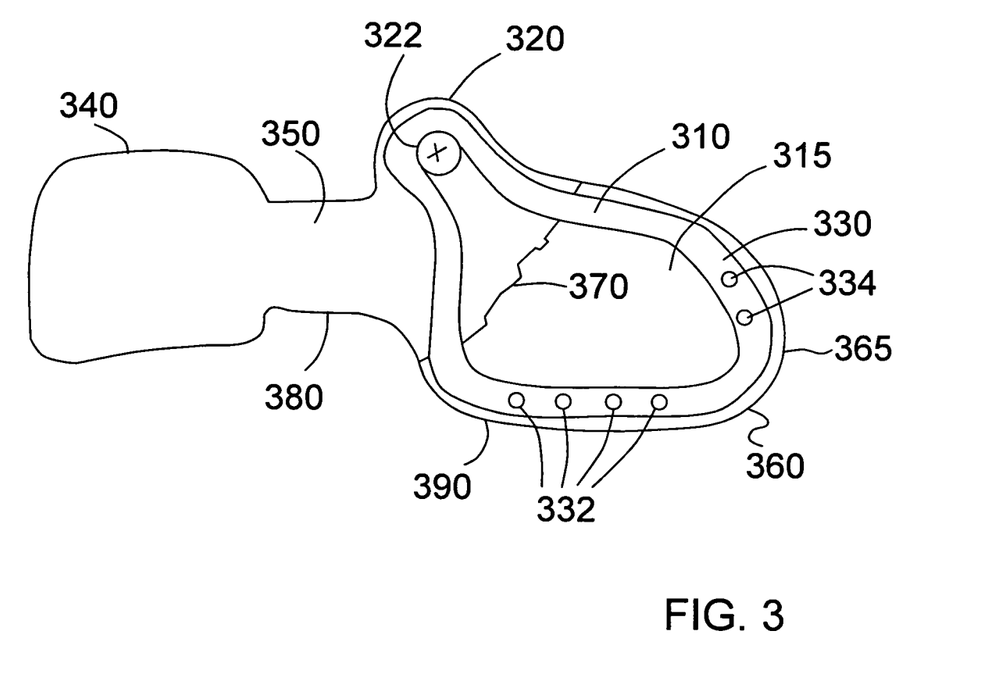
FIG. 3 is a perspective view of a plate attached to a pars area of a vertebra.

FIG. 3 is a perspective view 300 of a plate attached to a pars area of a vertebra 340. The vertebra 340 includes a pedicle 350 and a lamina 360, which includes a spinous, or transverse, process 365. The depicted vertebra has a fracture 370 in the pars area between the pedicle 350 and the lamina 360. When fractured, the vertebra 340 is fragmented into a vertebral fragment 380 that includes the pedicle 350, and a vertebral fragment 390 that includes the lamina 360.

A plate 310 used for rigid fixation of the fracture 370 is attached to the vertebra in order to rigidly fix the vertebral fragment 380 containing the pedicle 350 to the vertebral fragment 390 containing the lamina 360 in order to facilitate successful healing of the fracture 370.

The plate 310 includes a pedicle section 320 that is of a shape similar to the shape of the pedicle 350. The pedicle section 320 of the plate 310 includes a hole or opening that enables a screw 322 to fix the pedicle section 320 of the plate 310 to the pedicle 350. Additionally, in some examples the plate 310 may be attached to the vertebral fragment 380 at various different areas of the vertebral fragment 380 in addition to the manner depicted.

As shown, the pedicle section 320 of the plate 310 is shaped and/or is formed having a geometry that is similar to a shape and/or anatomical geometry of the pedicle 350. Shaping the pedicle section 320 in such a manner enables the plate 310 to conform to the area in which it is fixed, which allows for the plate to be placed within such a dense, complex area of a spinal column, among other benefits.

The plate 310 also includes a lamina section 330 that is of a shape similar to a shape and/or anatomical geometry of the lamina 360. The lamina section 330 of the plate 310 includes one or more attachment sections, includes attachment sections that facilitate using lamina screws 332 to attach the plate 310 to the lamina 360, attachment sections that facilitate using spinous process screws 334 to attach the plate 310 to the spinous process 365, and so on. Additionally, in some examples the plate 310 may be attached to the vertebral fragment 390 at various different areas of the vertebral fragment 390 in addition to the manner depicted.

As shown, the lamina section 330 of the plate 310 is shaped and/or is formed having a geometry that is similar to a shape and/or geometry of the lamina 360 and/or spinous process 365. Shaping the lamina section 330 in such a manner enables the plate 310 to conform to the area in which it is fixed, which allows for the plate to be placed within such a dense, complex area of a spinal column, among other benefits.

In certain embodiments, the plate 310 includes an opening 315 or inner portion that provides access to the fracture 370 within the pars area of the vertebra 340. That is, the plate 310 may be configured to give surgeons access to a fracture 370 in order to perform bone grafting procedures while the plate 310 rigidly maintains the vertebral fragments together, may be configured to allow for local vascular in-growth of the fracture 370, may be configured to enable access of the fracture 370 for post operation CT Scan imaging procedures, and so on.

Thus, in certain embodiments, the plate 310 includes an outer portion that is shaped similar to areas of a vertebra in which the plate attaches and is shaped similar to the areas of the vertebra in which the plate attaches, and an inner portion that enables access to a fractured or repaired area of the vertebra.

Determining the Size and/or Shape of the Pars Plate

In addition to conforming to the shape of the attachment areas of a vertebra, the plate, in certain embodiments, may also be formed of a size that conforms to the size of the attachment areas. In some cases, plates of differing sizes, such as sizes based on anatomical averages of sizes of the vertebra, may be formed. A left plate may be formed, a right plate may be formed, a bilateral plate may be formed, and so on. However, in some cases, a more specific sized and/or shaped plate may be required.

Figure 4:
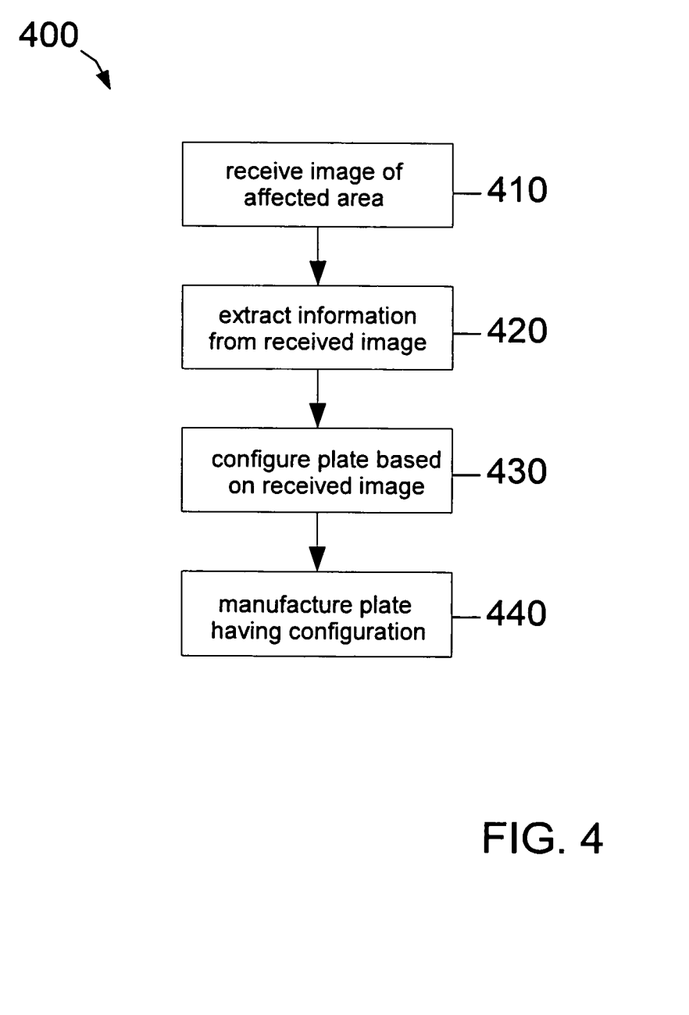
FIG. 4 is a flow diagram illustrating a routine for developing a plate used to rigidly fix a pedicle to a lamina.

In certain embodiments, the size and shape of a plate may be determined based on images or other information associated with the area in which the plate is to be attached. FIG. 4 is a flow diagram illustrating a routine 400 for configuring and manufacturing a plate used to rigidly fix a pedicle to a lamina.

FIG. 4 and the following discussion provide a brief, general description of a suitable computing environment in which a plate configuration system can be implemented. Although not required, aspects of the system are described in the general context of computer-executable instructions, such as routines executed by a general-purpose computer, e.g., a server computer, wireless device, or personal computer. Those skilled in the relevant art will appreciate that the system can be practiced with other communications, data processing, or computer system configurations, including: Internet appliances, network PCs, mini-computers, mainframe computers, medical computing devices, and the like. Indeed, the terms "computer" and "computing system" are generally used interchangeably herein, and refer to any of the above devices and systems, as well as any data processor.

Aspects of the system can be embodied in a special purpose computer or data processor that is specifically programmed, configured, or constructed to perform one or more of the computer-executable instructions or routines explained in detail herein. Aspects of the system can also be practiced in distributed computing environments where tasks or modules are performed by remote processing devices, which are linked through a communications network, such as a Local Area Network (LAN), Wide Area Network (WAN), Storage Area Network (SAN), Fibre Channel, or the Internet. In a distributed computing environment, program modules may be located in both local and remote memory storage devices.

Aspects of the system may be stored or distributed on computer-readable media, including magnetically or optically readable computer discs, hard-wired or preprogrammed chips (e.g., EEPROM semiconductor chips), nanotechnology memory, biological memory, or other tangible data storage media. Indeed, computer implemented instructions, data structures, screen displays, and other data under aspects of the system may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme). Those skilled in the relevant art will recognize that portions of the system reside on a server computer, while corresponding portions reside on a client computer, and thus, while certain hardware platforms are described herein, aspects of the system are equally applicable to nodes on a network.

In step 410, a system, such as a plate configuration system, receives an image or images of an affected area of a vertebra. The received images may be two-dimensional and/or three-dimensional images, providing information about images areas in all dimensions.

For example, the image may be a partial or full image of a vertebra, a partial or full image of a lamina area, a partial or full image of a pedicle area, a partial or full image of a fracture area, a partial or full image of a pars area, and so on. The image may be taken using a number of different imaging techniques, such as radiography (e.g., x-rays), X-Ray computed tomography (e.g. CT Scans), and so on.

In step 420, the system extracts information from the received image or images. For example, the system may extract information associated with sizes of areas of an affected vertebra, such as sizes of the vertebra, sizes of a pedicle, sizes of a lamina, sizes of a spinous process, sizes of the fractures area, sizes of the pars area, sizes associated with distances between the vertebra and other surrounding vertebrae, and so on. The system may extract other information, such as information associated with a shape of various areas of the vertebra, information associated with a bone density of various areas of the vertebra, and so on.

In step 430, the system configures a plate to be attached to the vertebra based on the extracted information. For example, the system may generate a schematic of a plate based on the size and/or shape information extracted from the received images.

In step 440, the system manufactures a plate according to the determined configuration. For example, the system manufactures a plate that is based on the generated schematic. Thus, the system may be utilizes to form plates that are optimizes in size and/or shape to the area in which they are to be attached. Such optimization may facilitate the use of plates in virtually every patient that suffers from Spondylolysis, such as very large or small patients, patients that have abnormal spinal column geometries, patients that have abnormal vertebra geometries, and so on.

Thus, in certain embodiments, the plates described herein further and expand upon the state of the art by providing devices that rigidly fix vertebral fragments together, improving over the conventional practice of using wires or other unsuitable fixation practices.

Other Plate Configurations

Figure 5A:
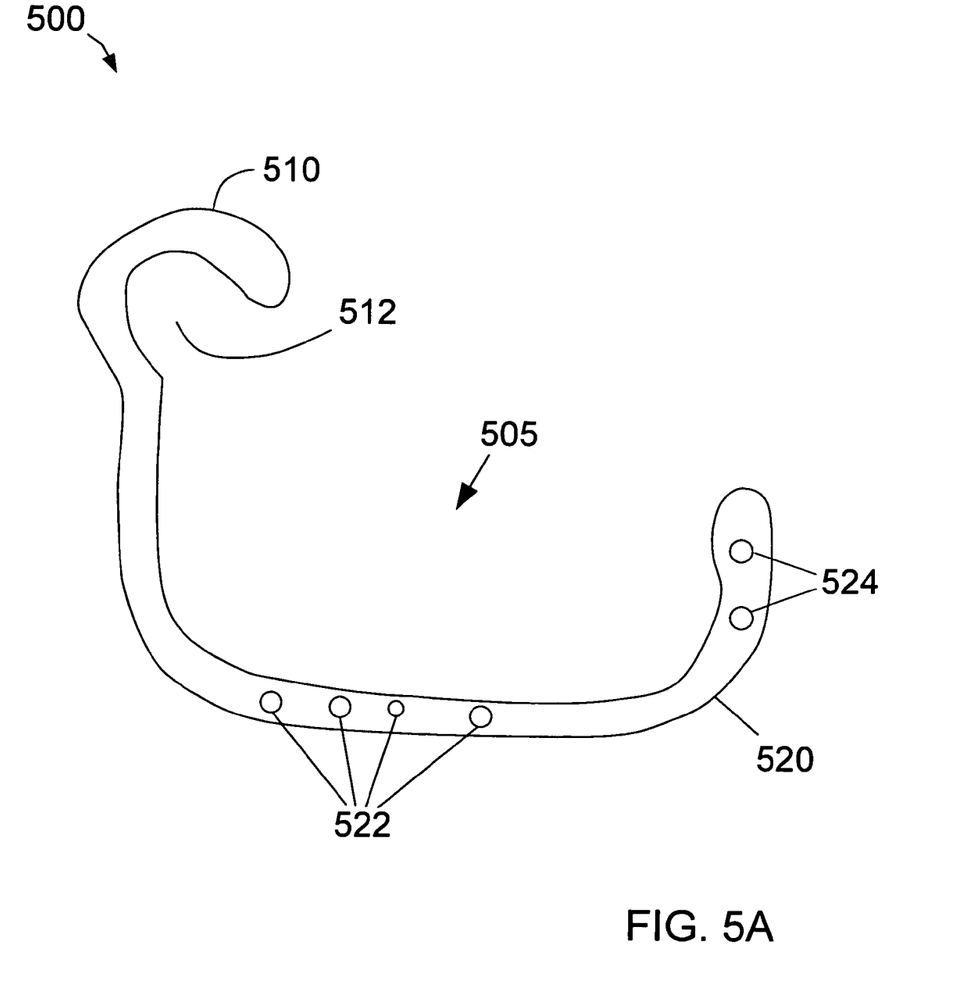
FIGS. 5A-5C are perspective views of various configurations of plates configured to be attached to a pars area of a vertebra.
Figure 5B:
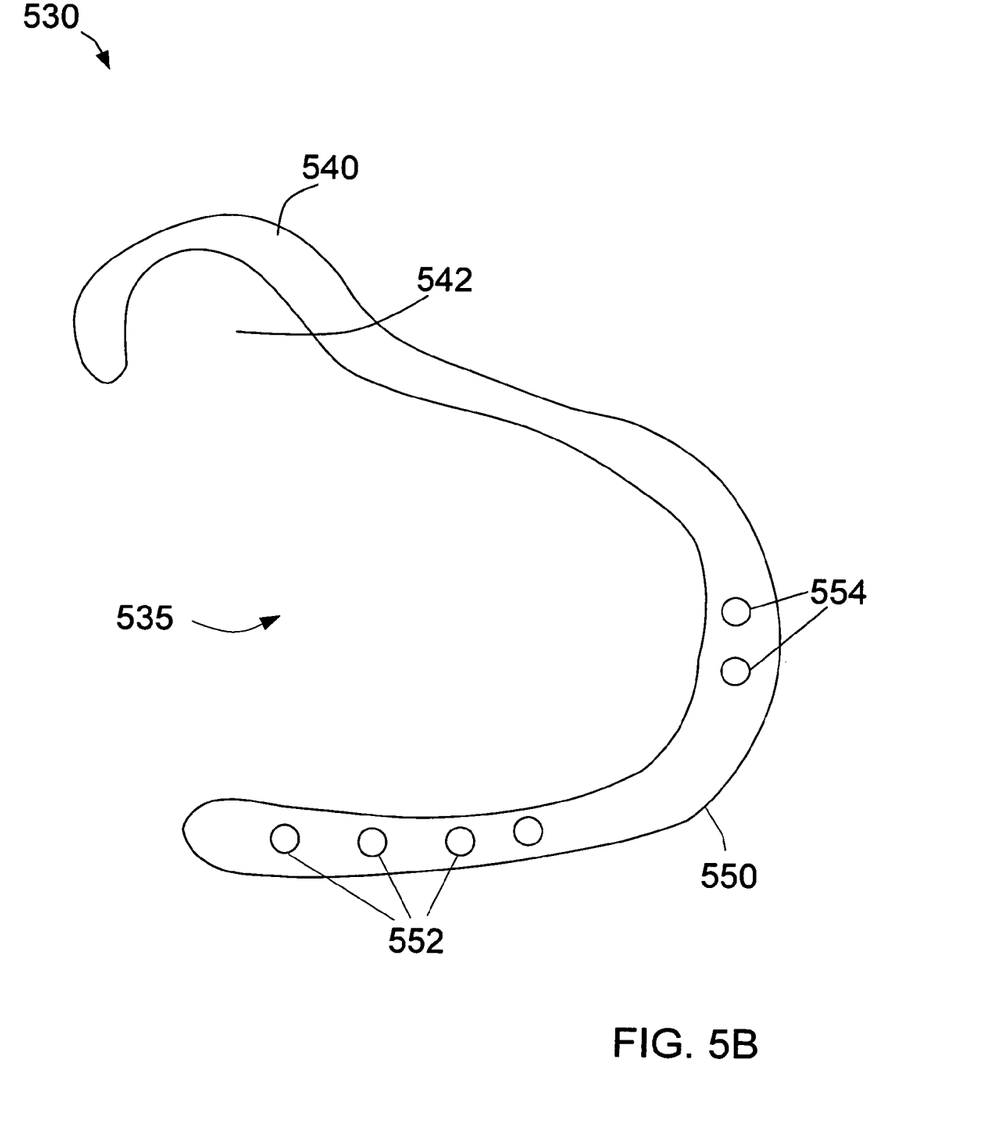
Figure 5C:
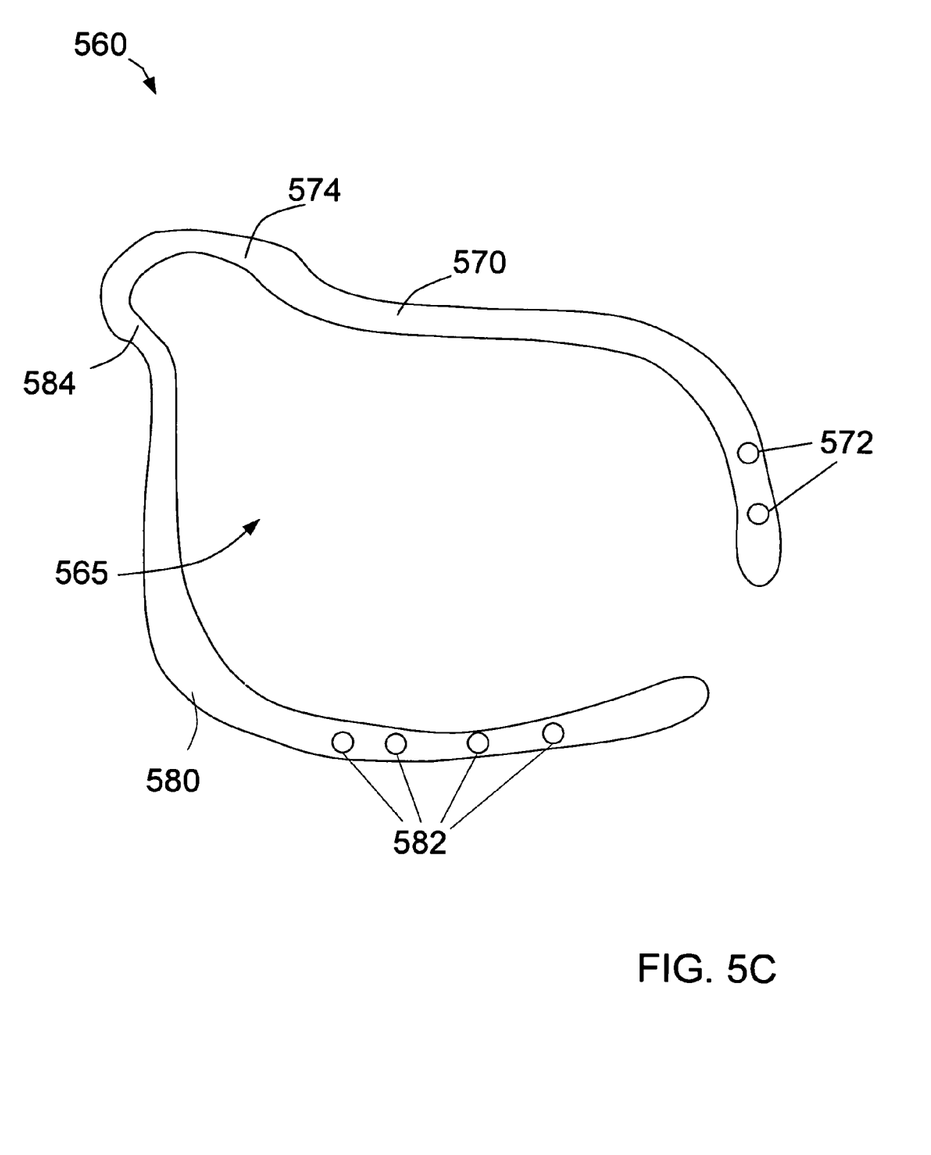

In alternative embodiments, the pars plate, such as plates 200 and 310, may be formed in a variety of different configurations. FIGS. 5A-5C are perspective views of various configurations of plates to be attached to a pars area of a vertebra.

FIG. 5A depicts a configuration in which a plate 500 is configured to run along a bottom portion of a lamina. The plate 500 includes a pedicle section 510, a lamina section 520, and an opening 505 or inner section. The pedicle section 510 includes or is shaped to include a hole 512 that facilitates use of a screw to attach the plate 500 to a pedicle of a vertebra. The lamina section includes lamina holes 522 and spinous process holes 524 that facilitate use of screws to attach the plate 500 to a lamina of a vertebra. The plate 500 is configured to provide an opening 505 or access area, which enables a fracture to be accessible when the plate 500 is attached to a vertebra.

FIG. 5B depicts a configuration in which a plate 530 is configured to run along a top portion of a lamina. The plate 530 includes a pedicle section 540, a lamina section 550, and an opening 535 or inner section. The pedicle section 540 includes or is shaped to include a hole 542 that facilitates use of a screw to attach the plate 530 to a pedicle of a vertebra. The lamina section includes lamina holes 552 and spinous process holes 554 that facilitate use of screws to attach the plate 530 to a lamina of a vertebra. The plate 530 is configured to provide an opening 535 or access area, which enables a fracture to be accessible when the plate 530 is attached to a vertebra.

FIG. 5C depicts a configuration in which a plate 560 is formed of two pieces, one formed to run along a bottom portion of a lamina, and one formed to run along a top portion of the lamina. The plate 560 includes an upper piece 570 having a pedicle section 574 that includes or is shaped to include an attachment point that facilitates use of a screw to attach the upper piece 570 to a pedicle of a vertebra, and a lamina section that includes lamina holes 572 that facilitate use of screws to attach the upper piece 570 to a lamina of a vertebra.

The plate 560 also includes a lower piece 580 having a pedicle section 584 that includes or is shaped to include an attachment point that facilitates use of a screw to attach the lower piece 580 to a pedicle of a vertebra, and a lamina section that includes lamina holes 582 that facilitate use of screws to attach the lower piece 580 to a lamina of a vertebra.

The plate 560 is configured to provide an opening 565 or access area, which enables a fracture to be accessible when the plate 560 is attached to a vertebra.

Of course, one of ordinary skill in the art will realize that other configurations may be utilized when forming plates to be attached to rigidly fix vertebral fragment together when repairing pars fractures. For example, plates having multiple (e.g., two or more) pieces may be formed, plates having various cross-sectional configurations may be formed, plates having various internal opening layouts may be formed, plates configure to treat dual fractures may be formed, and so on.

In certain embodiments, a plate may be part of an integrated support device within the spinal column. That is, the plate may be configured to attach to vertebral fragments associated with a pars fracture as well as surrounding vertebrae, in order to provide additional fixation during the healing process of the fracture, among other things.

Figure 6:
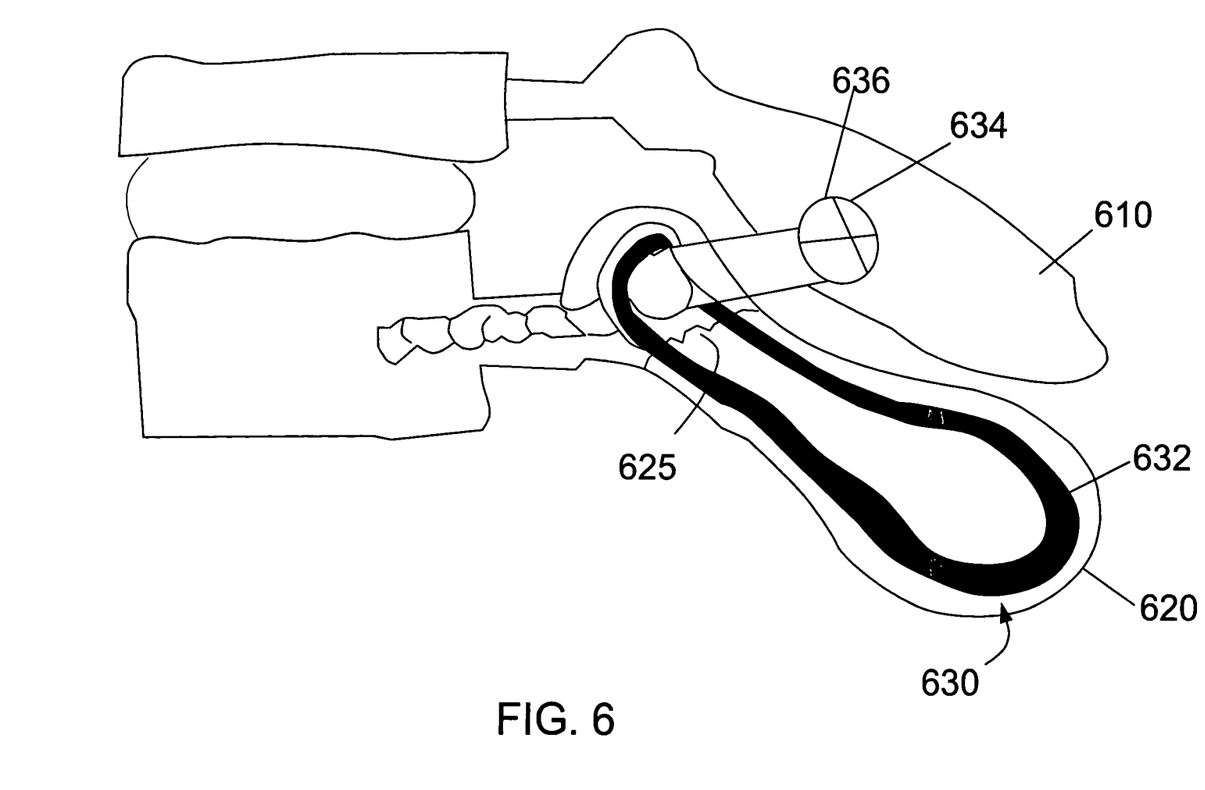
FIG. 6 is a perspective view of a support plate that includes a section configured to be attached to a pars area of a vertebra.

FIG. 6 depicts a view 600 of a support plate 630 that provides both fixation of vertebral fragments and attachment between an affected vertebra and surround vertebrae. The support plate 630 includes a fragment fixation section 632 and a support section 634. The support plate 630 utilizes the fragment fixation section 632, as described herein, to rigidly fix vertebral fragments of a vertebra 620 that contains a fracture 625. Furthermore, the support plate 630 includes a support section 634 that fixes the affected vertebra 620 to a surrounding vertebra 610 via the support plate, providing bilateral support to the affected vertebra while rigidly fixing the vertebral fragments, among other things.

The support section 634 may include an attachment portion 636 that attaches the plate 630, via the support section 634 to surrounding vertebrae. For example, the attachment portion 636 may include an opening that enables a screw to attach the support section 634 to vertebra 610, may include a wire or wiring mechanism that attaches the support section 634 to vertebra 610, may include a portion that facilitates fusion of the vertebra 610 to the plate 630 or to affected vertebra 620, and so on.

Thus, in certain embodiments, the support plate 600 furthers and expands upon the state of the art by providing a device that both rigidly fixes vertebral fragments together, improving over the conventional practice of using wires, and attaches an affected vertebra to surrounding vertebrae, improving over the conventional practice of fusing vertebrae together.

While certain aspects of the device are presented below in certain claim forms, the inventor contemplates the various aspects of the system in any number of claim forms. Accordingly, the inventor reserves the right to add additional claims after filing the application to pursue such additional claim forms for other aspects of the system.

I claim:

1. A bone plate configured to be attached to a single pedicle and a single lamina defining a single fractured pars area of a vertebra, the plate comprising:

a non-deformable monolithic structure having a three-dimensional shape similar to a three-dimensional shape of the single pedicle and the single lamina defining the fractured pars area of the vertebra, said monolithic structure defined by a continuous, unbroken elongate peripheral external rim and a continuous, unbroken elongate peripheral internal rim forming a closed loop, said external and internal rims are irregular along their entirety, the monolithic structure having an elongate upper surface and an opposing elongate lower bone contacting surface, said upper and lower elongate surfaces connecting said elongate external rim to said elongate internal rim and spacing the elongate rims from one another by an irregular distance of said surfaces, said entire internal rim and said entire external rim extend alongside each other, said continuous, unbroken peripheral external and internal rims define a pedicle plate section and a lamina plate section, wherein said external rim is structured to conform to a contour of the single pedicle and the single lamina, and said lower bone contacting surface of the structure of the bone plate is shaped to conform to a three dimensional geometry of the single pedicle and a three dimensional geometry of the single lamina, such that when the bone plate is implanted by affixing the structure of the plate to the single pedicle and the single lamina of the vertebra, said external rim of the bone plate extend alongside a periphery of the single pedicle and the single lamina of the vertebra;

wherein said upper surface and said lower bone contacting surface of the pedicle plate section lack screw holes therethrough and wherein said upper surface and said lower bone contacting surface of the lamina plate section include screw holes extending therethrough, said pedicle plate section structured to be fixed to the single pedicle, said external and internal rims of the pedicle plate section encircles most of a pedicle screw receiving hole having a crescent shape bounded mostly by the internal rim of the pedicle plate section and opening into a non-expandable narrow though gap defined between opposing portions of said internal rim that opens into a lamina open area encircled mostly by the internal and external rims of the lamina plate section, such that when the bone plate is implanted said plate is structured to overlie the fractured pars area; and wherein a total surface area between the external rim and the internal rim of the lamina plate portion is less than a total surface area of the lamina open area; and wherein a total surface area between opposing portions of the external rim of the pedicle plate section is smaller than a total surface area between opposing portions of the external rim of the lamina plate section; and wherein a dimension of the narrow through gap is smaller than a dimension of the pedicle screw receiving hole which is smaller than a dimension of the lamina open area.

2. The plate of claim 1, wherein each of said screw holes extending through said lamina plate section is adapted to receive a lamina screw to fix the laminar plate section to the single lamina.

3. The plate of claim 1, further comprising:

at least one spinous process screw receiving hole extends through said surfaces of said lamina plate section and adapted to receive at least one spinous process screw that fixes the lamina plate section to a spinous process.

* * * * *